United States Patent [19]
Demeter et al.

[11] Patent Number: 5,611,787
[45] Date of Patent: Mar. 18, 1997

[54] METHOD AND DEVICE FOR GASTRIC LINE INSERTION

[75] Inventors: Robert J. Demeter, Mooresville; Henry C. Bock; Dayong Gao, both of Indianapolis, all of Ind.

[73] Assignee: Methodist Hospital of Indiana, Inc., Indianapolis, Ind.

[21] Appl. No.: 322,579

[22] Filed: Oct. 13, 1994

[51] Int. Cl.$^6$ .................................................. A61M 31/00
[52] U.S. Cl. ........................................... 604/270; 604/280
[58] Field of Search .............................. 604/270, 43, 45, 604/283, 161, 164, 171, 280, 264

[56] References Cited

U.S. PATENT DOCUMENTS

| | | |
|---|---|---|
| 2,508,690 | 5/1950 | Schmerl . |
| 2,773,502 | 12/1956 | Kaslow et al. . |
| 3,155,097 | 11/1964 | Barron . |
| 3,528,429 | 9/1970 | Beal . |
| 3,683,890 | 8/1972 | Beal . |
| 4,134,405 | 1/1979 | Smit . |
| 4,239,040 | 12/1980 | Hosoya et al. . |
| 4,607,635 | 8/1986 | Heyden . |
| 4,637,389 | 1/1987 | Heyden . |
| 4,735,214 | 4/1988 | Berman . |
| 4,826,485 | 5/1989 | Johnson . |
| 4,979,947 | 12/1990 | Berman . |

OTHER PUBLICATIONS

Richard Pulling, The Right Place, *The Canadian Nurse*, pp. 29–30, (Feb. 1992).

*Primary Examiner*—Corrine M. McDermott
*Assistant Examiner*—N. Kent Gring
*Attorney, Agent, or Firm*—Barnes & Thornburg

[57] ABSTRACT

The present invention provides a method and device for placement of a gastric line in the digestive tract of a patient. A guide element is either formed integrally with the end of a gastric line or it is formed separately to be fixed on the end segment of a gastric line to reduce the flexibility of the gastric line segment and facilitate the positioning of the gastric line in a patient's digestive tract. The guide element is provided with means for slideably engaging a previously positioned transepiglottal guide line so that the guide element when engaged with the guide line, can be pushed down the guide line to position the gastric line in an esophageal or post-esophageal position. An optional mouthpiece is provided to receive and guide the gastric tube toward the middle of the posterior oral pharynx during insertion and to protect the gastric line from the biting surfaces of the teeth and maintain its position in the mouth after insertion.

19 Claims, 4 Drawing Sheets

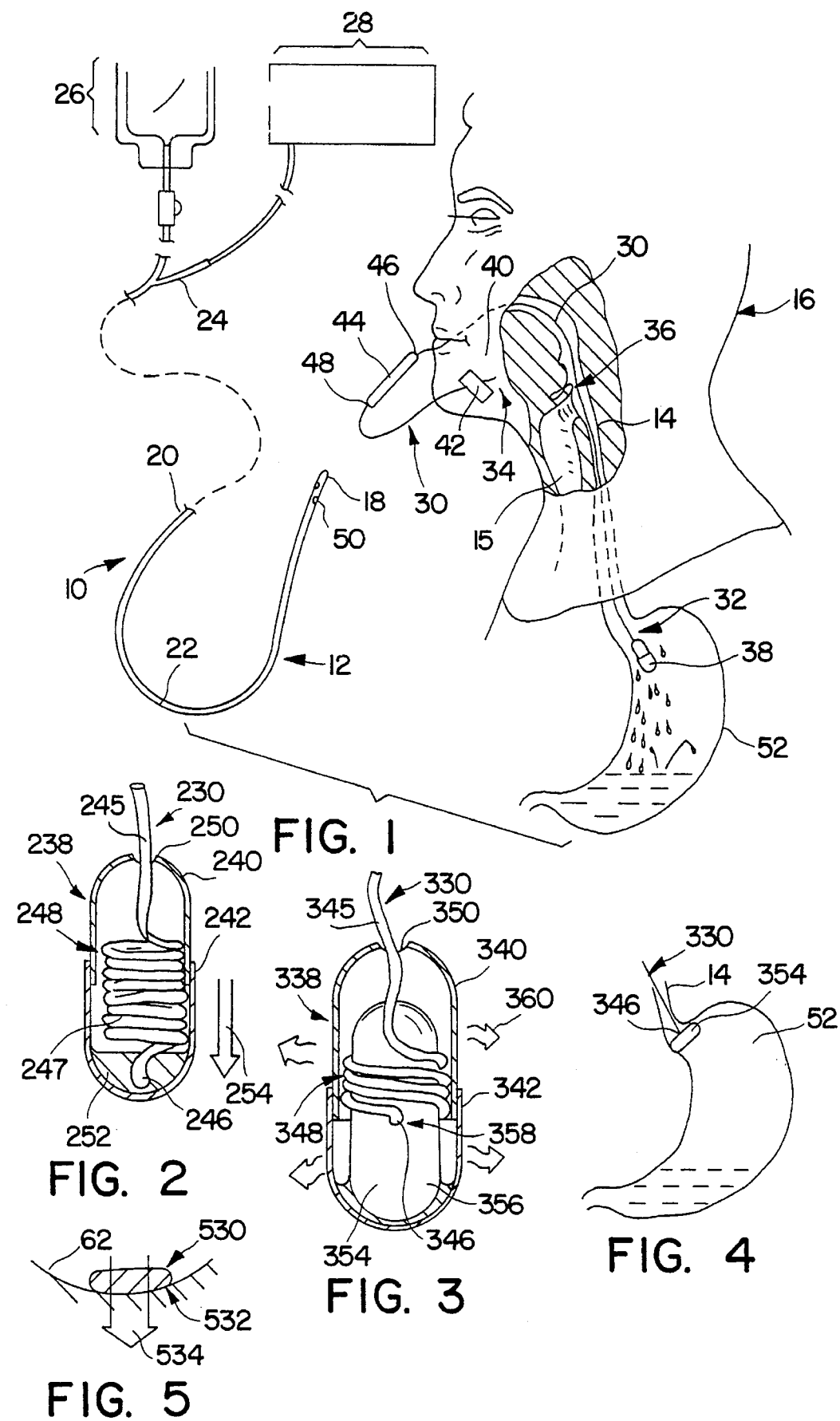

METHOD AND DEVICE FOR GASTRIC LINE INSERTION

FIELD OF THE INVENTION

The present invention relates to placement of gastric lines in the digestive tract of a patient. More particularly, the present invention is directed to a method and device making use of a transepiglottal guide line, a guide element for tracking said guide line, and optionally a mouthpiece to position a gastric line in an esophageal post-esophageal portion of the digestive tract.

BACKGROUND OF THE INVENTION

Gastro-intestinal devices designed for insertion into the digestive tract are commonly used in medical treatment. Such devices are used for removing gas and fluid from the gastro-intestinal tract, for performing diagnostic testing, and for the delivery of medications, fluids or nutrients into the gastro-intestinal tract. Typically, such gastro-intestinal devices are inserted by pushing the device through the oral cavity or the nasal passage into the esophagus of the patient. The devices generally include a flexible line or tube, designed to follow the contours of the digestive tract of the patient as it is inserted. However, the necessary flexibility of the line or tube also leads to difficulties during insertion of the device. As the flexible line or tube component is pushed into the pharynx of the patient, instead of remaining straight and passing into the esophagus it can coil in the back of the oropharynx. In addition, as the line or tube is inserted, following the contours of the pharyngeal surfaces, the inserted end of the gastric line tends to bend towards the trachea rather than the esophagus. Insertion procedures are further complicated by the fact that contact of the line or tube with structures of the oropharynx frequently induces a gag reflex in the patient. The speed and ease of the insertion procedure are critical to minimizing patient discomfort. Ideally gastric lines are quickly, yet carefully directed through the pharynx and into the esophagus while avoiding entry into the larynx. Gastric lines can also be inserted through the nostril. However, similar to the oral insertion protocol, successful placement of the gastric line through the nostril depends much on the skill of the physician—poor technique leads to extreme patient discomfort and tissue damage. For these and other reasons, current techniques for inserting tubes or lines of gastro-intestinal devices (hereinafter referred to generally as "gastric lines") require that the physician or technician possess a high level of skill.

One type of gastric line commonly inserted into the esophagus of patients is a gastro-intestinal tube for introducing or removing fluids. Gastro-intestinal tubes typically have a plurality of apertures located at or near the insert end of the tube. One additional disadvantage of current insertion methods is the tendency of the apertures to become clogged with mucus during the course of the insertion, or clogged with other matter present in the stomach.

Accordingly, there is a need for the development of new methods and devices which reduce the risk of inserting gastric lines into the trachea and which minimize patient discomfort caused by the insertion procedure.

One general object of this invention is to provide a method for inserting a flexible gastric line into the esophagus of a patient with minimal patient discomfort and with minimal risk of misdirection of the gastric line into the trachea.

Another object of this invention is to provide a gastric tube insertion kit which includes a guideline which can be easily located in a patient's digestive tract and used as a guide for gastric line insertion.

Still another object of the present invention is to provide a guide element which can be fixed in contact with a segment of a gastric line in a position at or near the inserted (gastric) end of the gastric line to decrease the flexibility of the contacted segment and to provide means for slideably engaging a pre-positioned transepiglottal guide line.

A further object of the invention is a mouthpiece for receiving and optionally guiding a gastric line through the oral cavity to minimize its contact with structures of the oropharynx, and retaining the gastric line in position in a patient's mouth, and protecting it from the biting surfaces of the teeth.

SUMMARY OF THE INVENTION

In one embodiment of the present invention there is provided a guide element formed to be fixed in contact with a segment of a gastric line at or near the end of the line to be inserted into a patient's digestive tract. When fixed on the gastric line, the guide element reduces the flexibility of at least a portion of the contacted gastric line segment to facilitate directing the inserted end of the line into the esophagus. The guide element is provided with means for slideably engaging and tracking a previously positioned transepiglottal guide line. The transepiglottal guide line is preferably positioned in a patient by having the patient swallow a bolus attached to the gastric end of the guide line with the other end extending from the patient's mouth. The end of the gastric line with the affixed guide element in slideably engagement with the guide line can be easily pushed down the guide line to a predetermined esophageal or post-esophageal position in a patient's digestive tract. Optionally in accordance with another embodiment of this invention, the guide line can be extended through the lumen of a gastric tube or the end of the gastric tube to be inserted can be modified to include an integrally formed guide element for slideable engagement with the guide line. Gastric line insertion and retention can be further facilitated by use of a mouthpiece to be positioned in a patient's mouth for receiving the gastric tube, guiding it toward the middle of the posterior oral pharynx, and protecting it from the biting surfaces of the teeth.

This invention is also directed to a gastric line insertion kit including a guide line, means for positioning one end of the guide line in a patient's stomach, and means for slideably engaging the gastric end of a gastric line with the pre-positioned guideline. Slideable engagement of a gastric tube with the guideline is accomplished by extending the guideline through the lumen of the gastric tube, forming the gastric end of the tube to include separate channel, bore or track for slideably receiving the guideline or by providing a separate guide element for positioning on the gastric end of the gastric tube.

Additional features and advantages of the present invention will become apparent to those skilled in the art upon consideration of the following detailed description of the preferred embodiments.

BRIEF DESCRIPTION OF THE DRAWINGS

FIG. 1 is a schematic representation illustrating use of a guide element in accordance with the present invention.

FIG. 2 is a transverse sectional view of a guide line deploying capsule for use in accordance with the present invention.

FIG. 3 is a transverse sectional view of an alternative embodiment of a guide line deploying capsule.

FIG. 4 is a sectional view of a transepiglottal guide line positioned in a patient.

FIG. 5 is an enlarged sectional view of a guide line in contact with a lumenal surface of the digestive tract.

DETAILED DESCRIPTION OF THE INVENTION

Figures 6A, 6B:
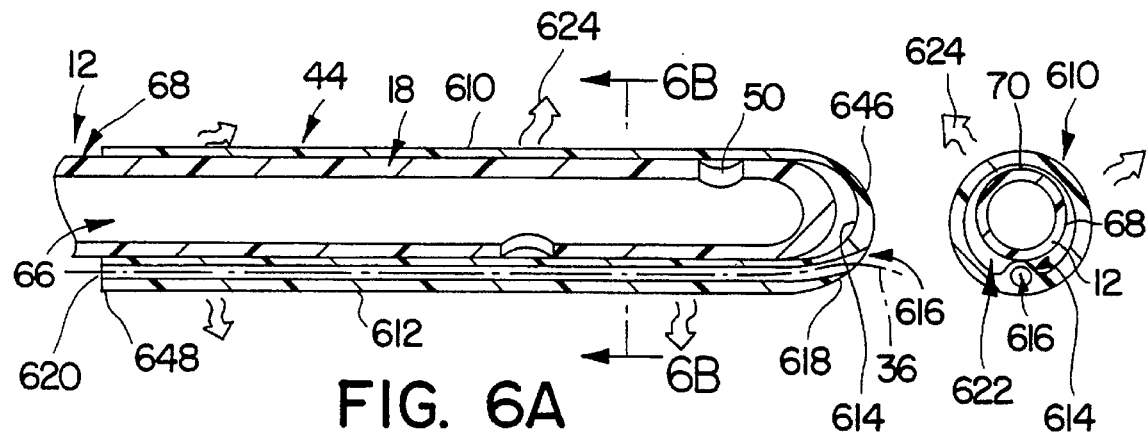
FIG. 6A is a transverse sectional view of a guide element in accordance with the present invention.
FIG. 6B is a cross sectional view along lines 6—6 of the embodiment of FIG. 6A.

The present invention is directed to a device and improved method for inserting a gastric line into an esophagus of the patient. The term "gastric line" as used herein is meant to encompass any medical-instrument-associated line or tube adapted for insertion into the esophagus of a patient. Medical instruments having lines or tubes intended for insertion into the esophagus include fiber optic devices for viewing the digestive tract, remotely operated tools for repairing or removing gastro-intestinal tissues, and stomachal, duodenal or intestinal tubes adapted for introducing or removing solid or fluid materials from the gastro-intestinal tract.

Gastric lines are typically made of flexible polymeric materials which allow the gastric line to follow the contours of the digestive tract as it is inserted in the patient. One element of the present invention is to reduce the flexibility of an inserted gastric end segment of the gastric line. The reduction in flexibility facilitates the insertion of the gastric line into the esophagus and decreases the chance of the gastric line entering into a trachea. Thus, in accordance with one embodiment of the present invention, a guide element is provided for being fixed in contact with the gastric line at or near the inserted end of the gastric line to reduce the flexibility of at least a portion of the segment of the gastric line contacted by the guide element and to provide means for slideable engagement with a prepositioned guide line. The guide element is formed to include a gastric end and an oppositely facing oral end and can further be in the form of a sleeve, a sheath or a channel construction designed for frictional and/or mechanical fixation on the gastric end of the gastric line. It can be formed from the same types of biocompatible polymers used in the art for gastric lines. Alternatively it can be formed of a material which is digestible or dissolvable in the digestive tract such as gelatin. With such construction, after insertion of the gastric line, the guide element dissolves in the stomach.

In one embodiment the guide element is formed as the sleeve or sheath having an outer surface and a lumenal surface, a gastric end and an opposite oral end. The lumenal surface provides means for fixing the guide element on the gastric line by frictional engagement with an outer surface of the gastric line. Optionally the lumenal surface of the sleeve may be tapered (and sized) to be frictionally engaged with the gastric line. Alternatively the lumenal surface of the guide element may comprise one or more radially inwardly extending protrusions, the protrusions providing frictional contact with the outer surface of the gastric line to fix the guide element in contact with the gastric line. The guide element, when positioned in contact with the gastric line, defines an annular volume between the outer surface of the gastric line and the lumenal surface of the guide line. The radially inwardly directed protrusions extend through the annular volume for frictional engagement with the outer surface of the guide line. Gastro-intestinal tubes adapted for introducing or removing solid or fluid materials from the digestive tract typically have one or more ports located at or near the gastric end segment of the gastro-intestinal tube. When the guide element is positioned on the gastric end of the tube at least a portion of the lumenal surface protrusions can engage the ports in the gastric end segment of the gastro-intestinal tube to provide additional frictional/mechanical contact to fix the guide element in contact with the gastric tube.

The guide element of the present invention can itself be further provided with a plurality of ports to allow fluid communication between the lumenal surface of the element and the outer surface of the element. The guide element having a plurality of ports is used in conjunction with the gastro-intestinal tube to reduce the flexibility of the inserted gastric end of the gastric tube without interfering with the flow of fluids into or out of the gastro-intestinal tube.

The guide element in accordance with this invention is also provided with means for slideably engaging the guide element with a prepositioned transepiglottal guide line. One means for engaging the guide element with the transepiglottal line comprises a bore for receiving the guide line. The bore can have a first guide line opening at or near the gastric end of the element and a second guide line opening at its opposite end. Alternatively, the second guide line opening may be located between the first guide line opening and the opposite end of the sleeve.

When the lumenal surface of the guide element is provided with radially inwardly directed protrusions for frictional engagement with the guide line, the guide element can be slideably engaged with transepiglottal guide line by receiving the line through the annular volume defined by the outer surface of the gastric line and the lumenal surface of the guide element. The gastric end of the guide element is either closed and provided with an aperture or open (i.e., a sleeve). The aperture or open end and the annular volume cooperate to define a passageway for slideably engaging the transepiglottal guide line.

Optionally the guide element can be formed as a sleeve or channel from a flexible material. The opposing edges of the material forming the sleeve or channel are biased together by the resiliency of the material and can be forced outwardly to increase the distance between the opposing edges. When a force is applied to separate the opposing edges, a gastric line can be passed between the opposing edges and placed in contact with the lumenal surfaces of the guide element. When the opposing edges return to their biased position upon removal of the sleeve/channel opening force, the guide element is fixed on the gastric line.

A construction of similar functionality can be provided for slideably engaging the guide line with the guide element or a modified gastric line. A longitudinal guide-line-receiving channel or groove is formed on the outer surface of the guide element or the gastric end of the gastric tube. The receiving channel or groove includes upper side walls which are biased to contact each other. The walls may be separated, however when applying a channel opening force, for example, by squeezing opposite lateral sides of the gastric tube or guide element. Squeezing the lateral sides opens the channel for receiving the guide line. Release of the lateral sides allow the biased channel walls to return to the "channel closed" position to provide a bore for slidable engagement with the guide line.

As mentioned above the means for slidable engagement with the guide line can comprise the lumen of the gastric line itself, it can be part of a fixed guide element, or the gastric end of the gastric line can be formed to include means for slidable engagement with the guide line as an integral part of its construction. Thus, the gastric end of the gastric line can be formed to include a separate bore, channel or groove for receiving the guide line in slidable engagement. Such is one preferred embodiment of the present invention.

In use, the transepiglottal guide line comprises a flexible element such as a string having a gastric end positioned in a esophageal or post esophageal region of the patient, an intermediate transepiglottal portion and a oral proximal end portion extending through the patient's mouth. In one preferred embodiment the guide line comprises dental floss or similar string-like material wherein the string-like material is of elliptical cross-section.

The transepiglottal guide line is positioned in a patient by having the patient swallow a bolus or capsule or capsule attached to the gastric end of the guide line while the opposite oral end of the guideline extends from the patient's mouth. Normal peristaltic action of the patient's upper gastro-intestinal tract will move the bolus and deploy the guide line into the stomach, thus positioning the guide line in a transepiglottal position. Because movement of the guide line against a oropharynx may cause a gag reflex in some patients, one preferred method for positioning the transepiglottal guide line comprises having the patient swallow the capsule containing a coiled portion of guide line within the capsule, wherein the coiled portion plays out of the capsule as the capsule moves down the patient's digestive tract. Preferably the guide line is attached to and wound on a spool or bolus which rotates freely within the capsule. Preferably the capsule has an aperture at one end through which the guide line plays out. The other end of the capsule preferably includes a weight, such as a gelatin plug. The weighted end serves the purpose of orientating the capsule as it is swallowed so that the apertured end of the capsule is positioned towards the mouth.

The oral end of the guide line may be fixed to a surface in the patient's mouth, or it may be fixed in a position outside the mouth of the patient. Preferably the capsule and the spool comprised digestible materials or dissolvable biocompatible materials. More preferably the capsule is a dissolvable/digestible gelatin capsule and the spool is a second smaller gelatin capsule. Attachment of the guide line to a mid-axial position on the spool orientates the spool to provide greater resistance to its removal from the stomach through the esophagus of the patient during the gastric line insertion procedure. This allows greater tension to be placed on the guide line. Once the transepiglottal guide line is positioned, it can serve as a guide for the insertion of the gastric line with affixed or integrally formed guide element into the esophagus of a patient.

Further in accordance with this invention there is provided a method for inserting the gastric line into the esophagus of the patient which method comprises the use of the transepiglottal guide line to guide the gastric line. Generally the method comprises the steps of positioning the transepiglottal guide line in the patient, slideably engaging the gastric line with the transepiglottal guide line either with or without use of a guide element depending on the construction of the gastric line and then pushing the gastric line along the slideably engaged transepiglottal guide line to direct the insertion of the gastric line into the esophagus of the patient.

Insertion and retention of a gastric line in accordance with the present invention is further facilitated by use of a mouthpiece adapted to receive the gastric line and to guide it and/or retain it in the mouth of the patient in a position least discomforting to the patient. The mouthpiece also functions to protect the gastric line from the biting surfaces of teeth.

The mouthpiece comprises a base having a posterior surface, lateral interior and lateral exterior surfaces and a teeth receiving channel between said lateral surfaces. The teeth receiving channel provides means for locating the device in the mouth of the patient. To increase the comfort of the patient, the mouthpiece may be further provided with means for holding an oral end of the gastric line in a position away from the corners of the mouth, and means for directing the gastric line toward the middle of the posterior oral pharynx to minimize its contact with the pharyngeal surfaces of the patient and thereby minimizing the gag reflex.

The gastric line can be received by a bore mouthpiece. The bore can be formed in the base or in a lateral extension formed on the lateral exterior surface of the base of the mouthpiece. The positioning of the lateral extension and placement of the bore openings on the base and lateral extension provide means for holding the gastric line in its preferred positions in the mouth. Alternatively where the mouthpiece is utilized simply for retaining the gastric line in position in the mouth, the gastric line can be received by a pair of opposed lateral projections on the lateral exterior surface of the base. These projections are positioned to fictionally fix the gastric line when the gastric line is positioned between the opposed lateral projections.

The mouthpiece can be coated or impregnated with, for example an anesthetic agent to reduce the gag reflex of the patient or otherwise to decrease the irritation caused by the insertion of the gastric line. Alternatively, or in addition, the mouthpiece can be coated or impregnated with a pharmaceutical agent for treating a patient condition unrelated to the insertion of the device, and used simply as a means of delivering an oral dosage form of a pharmaceutical.

FIG. 1 illustrates a device 10 in accordance with the present invention for facilitating placement of a gastric line 12 into the esophagus 14 and past a trachea 15 of a patient 16. The gastric line 12 itself includes an inserted gastric end segment 18 and an oral end 20. The gastric line 12 is illustrated as a gastro-intestinal tube 22 attached via a bifurcated tube 24 to a fluid administering container 26 and a pumping means 28. Additionally, the device 10 includes a guide line 30 having a gastric end 32 and an opposite oral end 34. The guide line 30 has a transepiglottal portion 36 and pre-positioned in the patient 16 and includes a capsule 38 attached to the gastric end 32. The opposite oral end 34 of the transepiglottal guide line extends outwardly from the patient 16 and is secured on a cheek 40 of the patient 16 with adhesive tape 42.

A guide element 44 having a gastric end 46 and an opposite end 48 is slideably engaged with the guide line 30. The inserted gastric end segment 18 of the gastric line 12 includes a plurality of apertures 50 and is fixed in contact with guide element 44. In use, the gastro-intestinal tube 22 and fixed guide element 44 are pushed along the engaged transepiglottal guide line 30 to direct the path of insertion of the gastric end segment 18 of the tube 22 through the esophagus 14 of the patient 16.

As best shown in FIG. 2, the capsule 38 may be formed as a two piece capsule 238 having opposite halves 240, 242, and a guide line 230 coiled therein. The guide line 230 itself includes a gastric end 246 and a portion 247 proximal to the gastric end 246 is wound in a single non-overlaying coil 248. Preferably, capsule 238 includes an aperture 250 through which extends a portion 245 of the guide line 230. The gastric end 246 is secured to the second half 242 of the capsule 238. Preferably, the capsule 238 is a dissolvable gelatin capsule, and most preferably contains a gelatin plug 252 positioned within the second half 242 to weight the capsule 238 in a downward direction 254.

An alternative embodiment of capsule 38, for use in positioning a guide line 30 in accordance with the present invention, is illustrated in FIG. 3. Two piece capsule 338 includes opposite halves 340, 342, a dissolvable gelatin bolus 354 positioned within the halves 340, 342, and a guide line 330. The guide line 330 is wound in a single nonoverlapping coil 348 about the outer surface 356 of the bolus 354 and the gastric end 346 is fixed to the central point 358 of the bolus 354. Preferably, capsule 338 is a dissolvable gelatin capsule which includes an aperture 350 formed in the first half 340 through which the guide line 330 extends. Gelatin bolus 354 is held within capsule 338 in a manner that allows the guide line 336 to play out through capsule aperture 350 of capsule 338. As best shown in FIG. 4 after the capsule 338 has been swallowed, halves 340, 342 dissolve to release the gelatin bolus 354 in the stomach 52 of the patient 16. The central attachment of the gastric end 346 to the gelatin bolus 354 allows the bolus 354 to become orientated in a position that permits the user to exert greater tension on guide line 330 without removal of the positioned guide line 336 from stomach 52.

A preferred embodiment of the guide line 30 (FIG. 1) for use in accordance with the present invention is illustrated in FIG. 5. The guide line 530 is formed as a string of elliptical cross-section, e.g., dental floss. The elliptical shape provides the guide line 530 with a flatten surface 532 for contacting patient tissues 62 and thus reduces the likelihood of damage to tissue 62 during positioning 534 and/or use of the guide line 530.

With reference to FIG. 6A, guide element 44 is fixed on the inserted end segment 18 of the gastric line 12. The gastric line 12 itself includes a lumen 66, an outer surface 68, and a plurality of apertures 50, extending between the lumen and the outer surface 68. Preferably the guide element 44 is formed as a sheath 610 having a gastric end 646 and an open opposite end 648. Sheath 610 further includes an outer surface 612, a lumenal surface 614, and a longitudinal bore 616 having a first opening 618 at or near gastric end 646 and a second opening 620 at opposite end 648 of the sheath 610. Longitudinal bore 616 provides means for slideably engaging sheath 610 with the guide line 30 (see FIG. 1).

With reference to FIG. 6B, the exterior surface 68 of gastric line 12 contacts the lumenal surface 614 of sheath 610 at contact sites 70 providing frictional engagement with sheath 610 on gastric line 12. Passageways 622 are formed between the outer surface 68 of gastric line 12 and the lumenal surface 614 of sheath 610 wherever the outer surface 68 of gastric line 12 does not contact the lumenal surface 614 of sheath 610. Advantageously, fluids 624 introduced into the lumen 66 of gastric line 12 can pass through gastric line apertures 50, enter passageway 622 and into the environment surrounding sheath 610. Sheath 610 may include a plurality of ports (not shown) to allow fluid communication between the lumenal surface 614 of the sheath 610 and the outer surface 612 of the sheath 610.

Figures 7A, 7B:
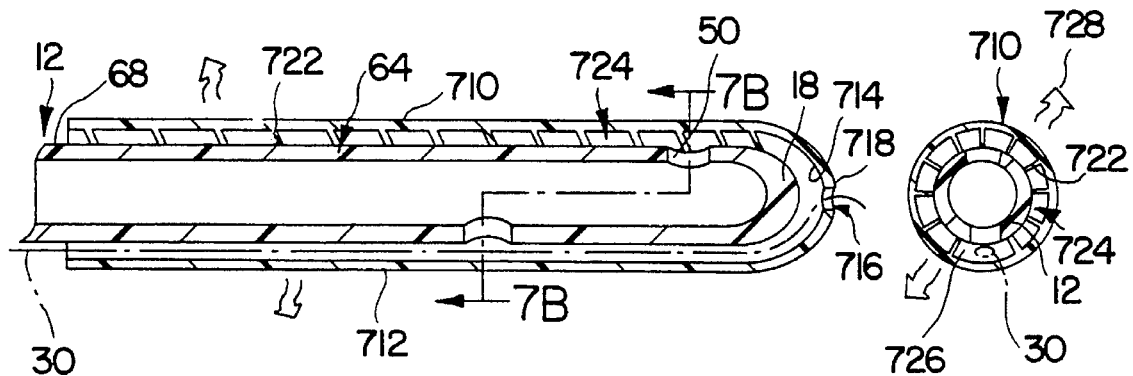
FIG. 7A is a transverse sectional view of an alternative embodiment of a guide element in accordance with the present invention.
FIG. 7B is a cross sectional view along lines 7—7 of the embodiment of FIG. 7A.

An alternative embodiment of the guide element 44 in accordance with the present invention is illustrated in FIGS. 7A and 7B. Sheath 710 is fixed on the inserted end segment 18 of gastric line 12. Sleeve 710 includes an outer surface 712, a lumenal surface 714, port 716 at gastric end 718, and a plurality of radially inwardly directed protrusions 722 that frictionally contact the outer surface 68 of gastric line 12. The outer surface 68 of gastric line 12 and the lumenal surface 714 of sheath 710 define an annular volume 724 with the radially inwardly directed protrusions 722 extending through annular volume 724. Inwardly directed protrusions 722 provide frictional engagement with gastric line 12 which fix the sleeve 710 on the gastric line 12. Annular volume 724 in combination with port 716 provide a passageway 726 for slideably engaging the sheath 710 with guide line 30. Fluid 728 introduced into the line 12 can pass through the apertures 50 and exit into the environment surrounding the sleeve 710.

Figures 8, 9:
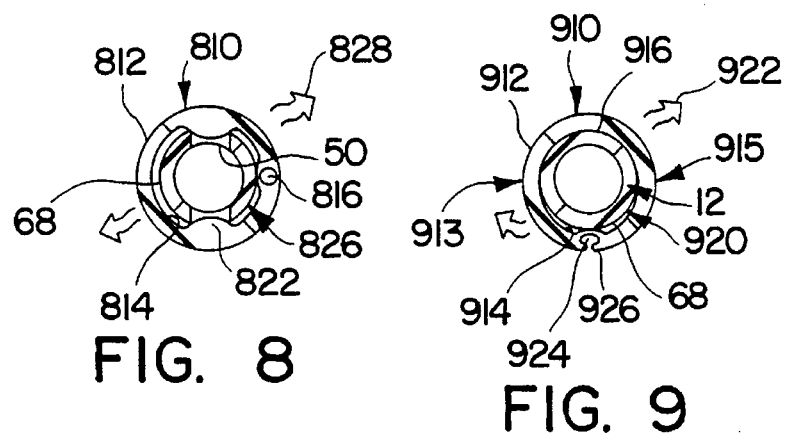
FIG. 8 is a cross sectional view similar to the view of FIG. 7B of a third embodiment of a guide element in accordance with the present invention.
FIG. 9 is a cross sectional view similar to the view of FIG. 7B of a fourth embodiment of a guide element in accordance with the present invention.

An additional embodiment of the guide element 44, in accordance with the present invention, is illustrated in FIG. 8. Guide element 810 includes an outer surface 812 and a lumenal surface 814 with inwardly directed protrusions 822 which extend to engage apertures 50 to fix guide element 810 on the gastric line 12. Passageways 826 are formed between the outer surface 68 of gastric line 12 and the lumenal surface 814 of guide element 810 wherever the outer surface 68 fails to contact the lumenal surface 814 of guide element 810. Fluids 828 introduced into gastric line 12 can pass through gastro-intestinal tube apertures 50, not blocked by inwardly directed protrusions 822, to enter passageway 826 and exit into the environment surrounding guide element 810. Guide element 810 is further provided with a longitudinal bore 816 providing means for slideably engaging guide element 810 with guide line 30.

An additional embodiment of the guide element 44 in accordance with the present invention is illustrated in FIG. 9. Guide element 910 is fixed on gastric line 12. The outer surface 68 of the gastric line 12 contacts the lumenal surface 914 of guide element 910 at multiple contact sites 916 providing frictional engagement to fix guide element 910 on gastric line 12. Passageways 920 are formed between the outer surface 68 of gastric line 12 and the lumenal surface 94 of guide element 910 wherever the outer surface 68 does not contact the lumenal surface 914. Advantageously, fluids 922 introduced into gastric line 12 can pass through gastrointestinal tube apertures 50, enter passageway 920 and exit into the environment surrounding guide element 910. Guide element 910 is further provided with a longitudinal groove 924 on outer surface 912 of guide element 910, and groove extensions 926 which extend from the outer surface 912 of the guide element 910 over longitudinal groove 924, providing means for slideably engaging guide element 910 to a guide line 30. Groove 924 can be opened to receive a guide line by application of guide-element-deforming pressure to opposite lateral sides 913, 915 of guide element 910.

Figure 10A:
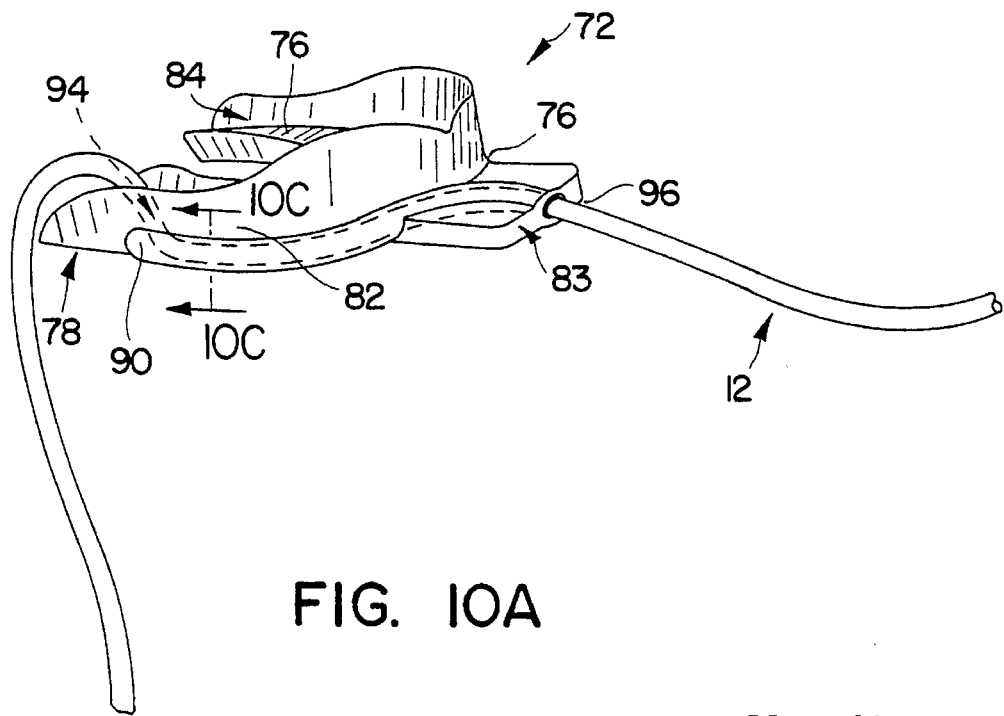
FIG. 10A is a perspective view of a mouthpiece optionally used for positioning and guiding insertion of a gastric line in accordance with this invention.
Figure 10C:
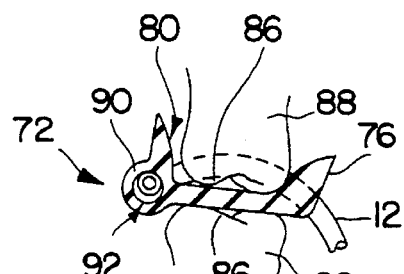
FIG. 10C is a sectional view along lines 10—10 of the embodiment of FIG. 10A.
Figure 10B:
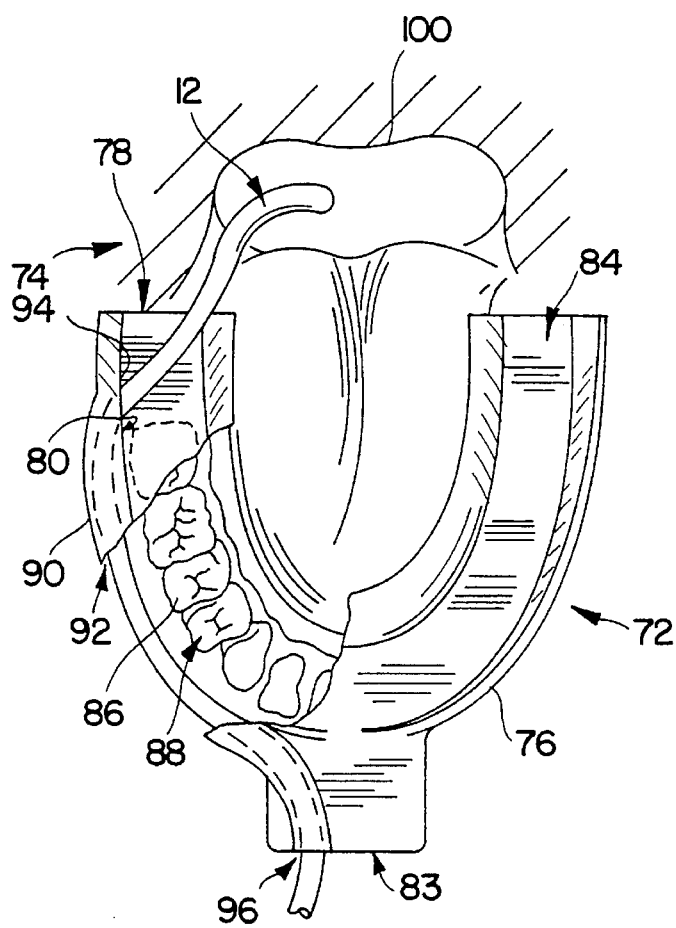
FIG. 10B is a top sectional view of the mouthpiece of FIG. 10A, positioned in the mouth of a patient.

A mouthpiece 72 for maintaining the position of a gastric line 12 in the mouth 74 of a patient in accordance with the present invention is illustrated in FIG. 10A, 10B and 10C. Referring to those Figures mouthpiece 72 includes a base 76 having a posterior surface 78, a lateral interior surface 80, a lateral exterior surface 82, and a teeth receiving channel 84 for positioning mouthpiece 72 in the mouth 74 of a patient 16 and preventing the biting surfaces 86 of the teeth 88 from contacting gastric line 12. Base 76 is provided with a lateral extension 90 which includes a bore 92 having a first opening 94 on the lateral interior surface 80 or the posterior surface 78 (FIG. 11) of the base 76 and a second opening 96 on the front exterior surface 83 of the base 76. The diameter of bore 92 is large enough to allow insertion of a gastric line 12. First opening 94 of bore 92 positions the gastric line 12 away from contact with the surface 100 of the pharynx (see FIG. 10B). The second opening 96 of bore 92 positions gastric line 12 away from corners of the mouth (not shown). As shown in FIG. 10C, the bore 92 which extends through the lateral extension 90, positions gastric line 12 in a lateral position in the oral cavity away from the biting surfaces 86 of the patient's teeth 90.

Figure 11:
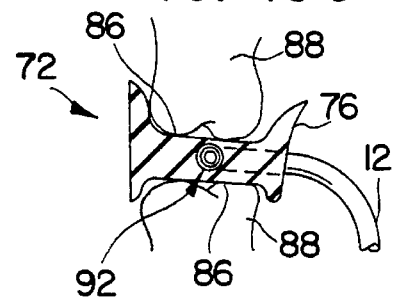
FIG. 11 is a sectional view similar to the view of FIG. 10C of an alternative embodiment of a retaining device.

In an alternative embodiment of the present invention illustrated in FIG. 11, the base 76 of the mouthpiece 72 includes a bore 92 which passes through the portion of base 76 located between the patient's upper and lower teeth 88 when the mouthpiece 72 is positioned in the mouth 74 of the patient. The bore 92 is of a diameter large enough to receive gastric line 12, and protect gastric line 12 from the biting surfaces 86 of the patient's teeth 88. Bore 92 can be lubricated to facilitate insertion of gastric line 12.

Figure 12A:
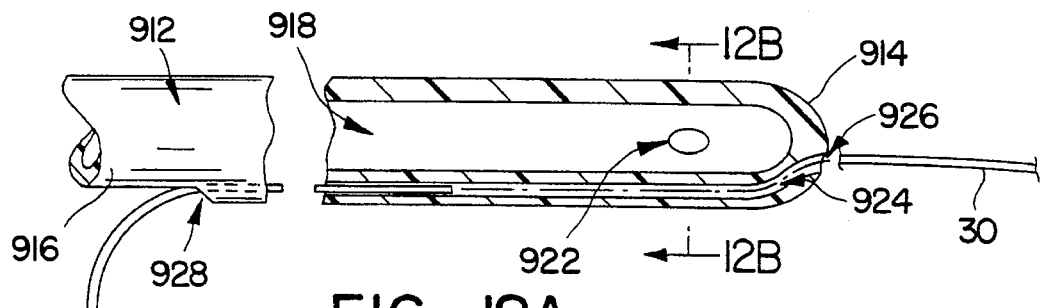
FIG. 12A is a transverse sectional view of a gastric line having the guide element formed as an integral part of the gastric line.
Figure 12B:
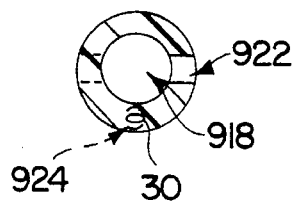
FIG. 12B is a sectional view along lines 12—12 of the embodiment of FIG. 12A.

FIGS. 12A and 12B illustrate one preferred embodiment of the present invention wherein the guide element is formed as an integral part a gastric line 912. Gastric line 912 is provided with a longitudinal bore 924 having a first opening 926 at or near the inserted gastric end segment 914 of the gastric line 912 and a second opening 928. Longitudinal bore 924 provides means for slideably engaging the gastric line 912 with the guide line 30. The end segment of a gastric line can be formed to include other means for providing slidable engagement with a guide line. For example, it can be formed to include a channel comparable to that shown on the guide element illustrated in FIG. 9, which is biased in a channel-closed position and subject to opening for receipt of a segment of guide line by application of a gastric line deforming force to the lateral sides of the gastric line. Alternatively the gastric end of the gastric tube can be open and the guide line can be extended through the lumen of the gastric tube.

Figure 13:
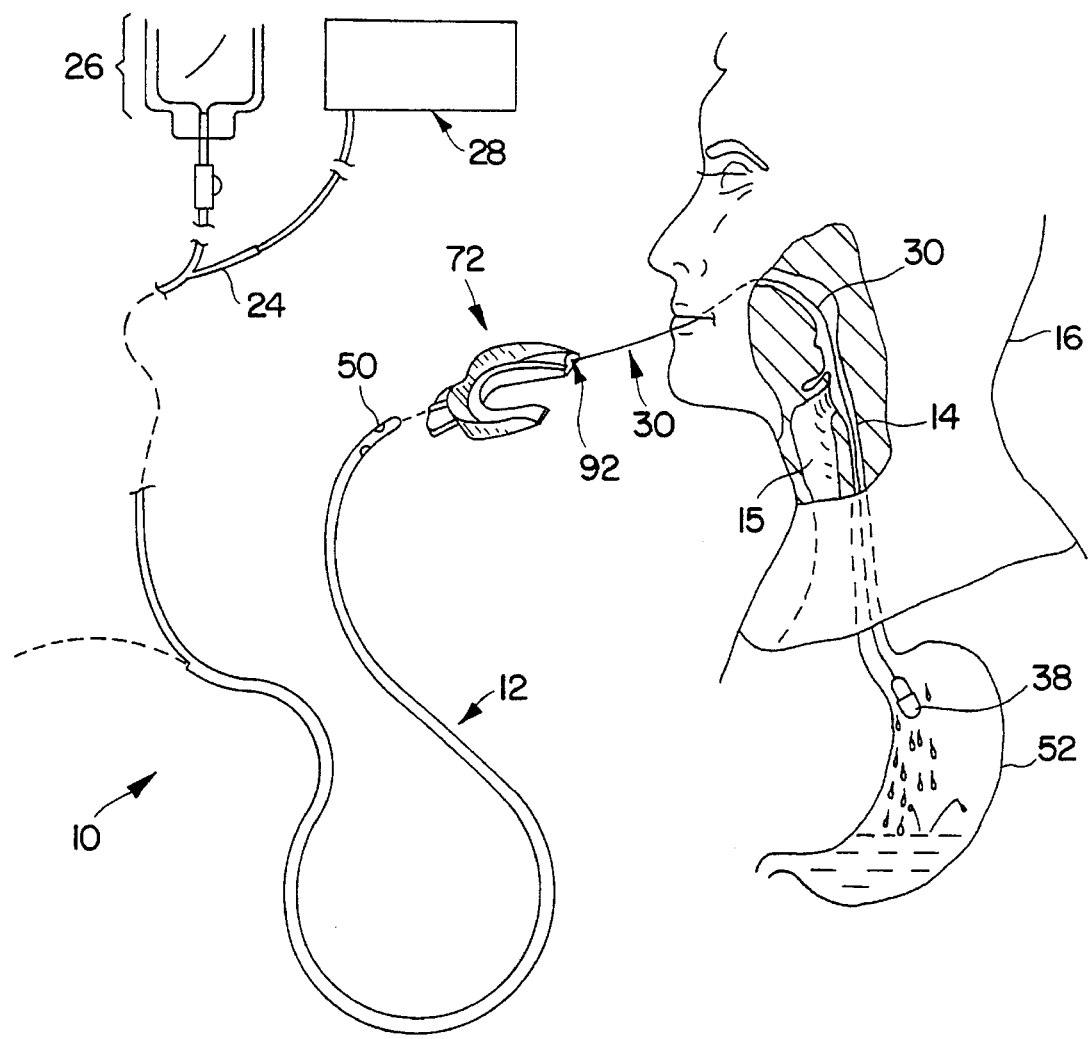
FIG. 13 is a schematic representation illustrating use of a modified gastric tube and mouthpiece in accordance with the present invention.

With reference to FIG. 13, mouthpiece 72 is used with guide line 30 having integrally formed guide element to guide the gastric line 12 into the esophagus 14 of the patient 16. The guide line 30 extends from the stomach 52 of the patient 16 and through both the bore 92 of mouthpiece 72 and a guide line engaging portion of the gastric line 12, thus slideably engaging the line 12 to the guide line 30. The gastric line 12 is then pushed along guide line 30 through the bore 92 formed in the mouthpiece 72, into the oral cavity, and into the esophagus 14.

Although the invention has been described in detail with reference to certain preferred embodiments, variations and modifications exist within the scope and spirit of the invention as described and defined in the following claims.

We claim:

1. A gastric tube insertion kit comprising
   a flexible gastric tube having a gastric end and an oral end and a lumen extending from said gastric end to said oral end;
   a guide line having a gastric end and an opposite oral end, said guide line extending through the lumen of the gastric tube so that the oral end of said guide line extends from the oral end of said gastric tube and the gastric end of said guide line extends from the gastric end of said gastric tube; and
   a bolus attached to the gastric end of the guide line for locating the gastric end of the guide line in the stomach, wherein said bolus is a capsule containing a portion of the guide line proximal to its gastric end.

2. The kit of claim 1 wherein the capsule has an aperture through which the guide line plays out as the capsule is swallowed and moves down the digestive tract.

3. The kit of claim 2 wherein the guide line is wound on a spool in the capsule.

4. The kit of claim 1 wherein the gastric tube is constructed to have a segment of reduced flexibility, said segment including the gastric end of the tube.

5. The kit of claim 1 further comprising a mouthpiece with means for receiving the gastric tube and guiding the tube toward the middle of the posterior pharynx.

6. The kit of claim 5 wherein the mouthpiece is adapted to be affixed to teeth or gums.

7. The kit of claim 5 wherein the mouthpiece includes means for protecting the gastric tube from the biting surfaces of the teeth.

8. A gastric line insertion kit comprising
   a guide line having a gastric end and an opposite oral end;
   a flexible gastric line having a gastric end and an oral end, said gastric end including means for slideably engaging the gastric line with the guide line; and
   a bolus attached to the gastric end of the guide line for locating the gastric end of the guide line in the stomach, wherein the bolus is a capsule containing a portion of the guide line proximal to its gastric end.

9. The kit of claim 8 wherein the means for slideably engaging the gastric line with the guide line comprises a longitudinal bore having a first opening at or near the gastric end of the gastric line and a second opening between the oral end of the gastric line and the first opening.

10. The kit of claim 9 wherein the gastric line is constructed to have a segment of reduced flexibility, said segment including the gastric end of the gastric line.

11. The kit of claim 9 further comprising a mouthpiece with means for receiving the gastric line and guiding the line toward the middle of the posterior pharynx.

12. The kit of claim 11 wherein the mouthpiece is adapted to the affixed to teeth or gums.

13. The kit of claim 11 wherein the mouthpiece includes means for protecting the gastric line from the biting surfaces of the teeth.

14. The kit of claim 8 wherein the capsule has an aperture through which the guide line plays out as the capsule is swallowed and moves down the digestive tract.

15. The kit of claim 14 wherein the guide line is wound on a spool in the capsule.

16. A method for inserting a flexible gastric line into the esophagus of a patient, said gastric line having a gastric end for insertion into the patient and an oral end, said method comprising the steps of

- positioning a guide line in a patient so the guide line has an oral end, an intermediate transepiglottal portion, and a gastric end, wherein the guide line is positioned by having the patient swallow a bioerodable bolus attached to the guide line;
- slideably engaging a guide element at or near the oral end of the guide line and fixing the guide element in contact with a segment of a gastric line at or near the gastric end of the gastric line; and
- pushing the gastric line and the fixed guide element along the engaged guide line to direct the insertion of the gastric line into the esophagus of the patient.

17. A method for inserting a flexible gastric line into the esophagus of a patient, said gastric line having a gastric end for insertion into the patient and an oral proximal end, said method comprising the steps of

- positioning a guide line in a patient so the guide line has an oral end, an intermediate transepiglottal portion, and a gastric end;
- slideably engaging the gastric end of the gastric line with the guide line;
- positioning a mouthpiece for receiving and guiding the gastric line in the patient's mouth;
- pushing the gastric line through the mouthpiece and along the slideably engaged guideline to insert the gastric line into the esophagus of the patient.

18. A kit for use in facilitating the insertion of a gastric line, said kit comprising

- a guide line having a gastric end and an oral end and means for locating the gastric end of the guide line in the stomach;
- a guide element adapted to be fixed in contact with a segment of the gastric line and slideably engaged with the guide line; and
- a mouthpiece capable of holding the gastric line in position in a patient's mouth.

19. The kit of claim 18, wherein the means for locating the gastric end of the guide line in the stomach is a capsule to be swallowed by a patient, said capsule having an aperture through which the guide line plays out as the capsule is swallowed and moves down the digestive tract of a patient.

* * * * *